(12) United States Patent
McDonald

(10) Patent No.: US 10,898,682 B2
(45) Date of Patent: Jan. 26, 2021

(54) MICROTUBE GUIDE

(71) Applicant: Michael B. McDonald, Cordova, TN (US)

(72) Inventor: Michael B. McDonald, Cordova, TN (US)

(*) Notice: Subject to any disclaimer, the term of this patent is extended or adjusted under 35 U.S.C. 154(b) by 0 days.

(21) Appl. No.: 15/602,463

(22) Filed: May 23, 2017

(65) Prior Publication Data

US 2017/0252538 A1 Sep. 7, 2017

Related U.S. Application Data

(63) Continuation-in-part of application No. 15/445,272, filed on Feb. 28, 2017.

(60) Provisional application No. 62/340,111, filed on May 23, 2016, provisional application No. 62/301,270, filed on Feb. 29, 2016.

(51) Int. Cl.
*A61M 25/01* (2006.01)
*A61M 25/09* (2006.01)
*A61F 2/24* (2006.01)
*A61M 25/00* (2006.01)

(52) U.S. Cl.
CPC .. *A61M 25/0102* (2013.01); *A61M 25/09025* (2013.01); *A61M 25/09041* (2013.01); *A61F 2/2427* (2013.01); *A61M 25/0041* (2013.01); *A61M 2025/0042* (2013.01)

(58) Field of Classification Search
CPC ........ A61M 25/0102; A61M 25/09025; A61M 25/09041
USPC ........................................................ 600/585
See application file for complete search history.

(56) References Cited

U.S. PATENT DOCUMENTS

| | | | | |
|---|---|---|---|---|
| 4,854,330 A | * | 8/1989 | Evans, III | A61M 25/09 600/585 |
| 6,206,834 B1 | * | 3/2001 | Schwager | A61B 5/0215 600/485 |
| 2009/0275862 A1 | * | 11/2009 | Elsesser | A61M 25/09 600/585 |
| 2010/0256528 A1 | * | 10/2010 | Lippert | A61M 25/0013 600/585 |
| 2014/0155994 A1 | * | 6/2014 | McDonald | A61F 2/2427 623/2.11 |

* cited by examiner

*Primary Examiner* — Daniel L Cerioni
(74) *Attorney, Agent, or Firm* — Angela Holt; Bradley Arant Boult Cummings LLP

(57) ABSTRACT

A microtube guide has a microtube combined with a free-floating and removable core. The microtube is generally hollow with a tube shaft and a distal ring, the tube shaft and the distal ring formed from flexible plastic. The distal ring is conformable to the core and straightenable for insertion into a patient's body, and deploys when the core is withdrawn to form a loop. The core is received by the microtube and is configured to advance into the distal ring to cause a diameter of the distal ring to expand, retract, or straighten. The distal ring diameter is thus adjustable by the user.

8 Claims, 3 Drawing Sheets

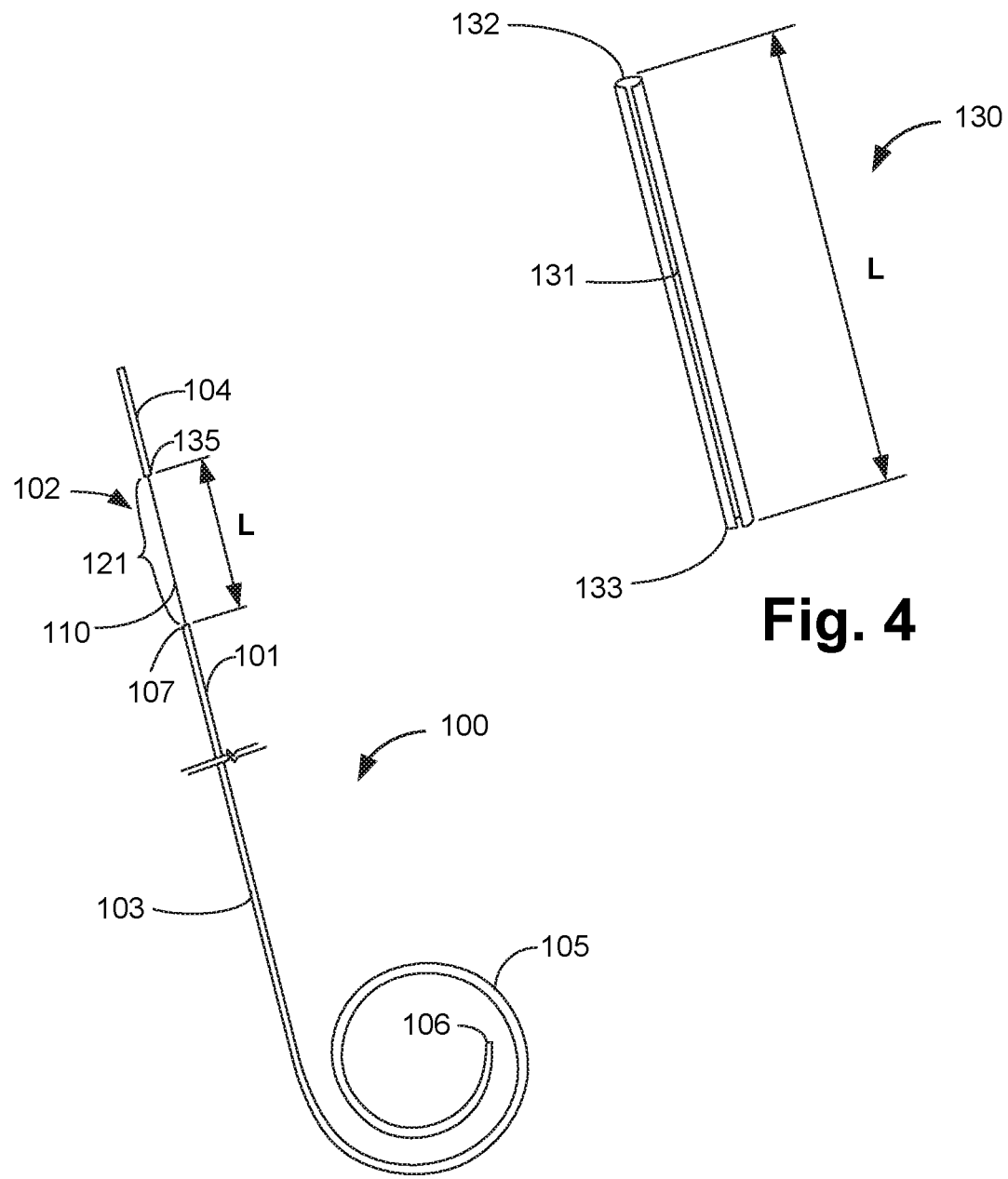

MICROTUBE GUIDE

REFERENCE TO RELATED APPLICATIONS

This application claims priority to Provisional Patent Application U.S. Ser. No. 62/340,111, entitled "Microtube Guide" and filed on May 23, 2016, which is fully incorporated herein by reference. This application further is a continuation-in-part of, and claims priority to, U.S. Non-Provisional application Ser. No. 15/445,272, entitled "TAVR Valve Guidewire and Guidetube with Adjustable Distal Loop," and filed on Feb. 28, 2017, which claims priority to U.S. Provisional Patent Application Ser. No. 62/301,270, entitled "TAVR Valve Guidewire and Guidetube with Adjustable Distal Loop" and filed on Feb. 29, 2016. These patent applications are fully incorporated herein by reference.

BACKGROUND AND SUMMARY

Guidewires, tiny wires designed to navigate vessels within the body, are used in a vast array of medical procedures. After a guidewire is advanced to its desired treatment site, the guidewire acts as a guide that larger catheters can rapidly follow for advancement to the treatment site.

Most currently-used guidewires are constructed of a solid wire or fixed core or slightly-movable core wrapped with wire. These wires have a set flexural strength (flexural modulus) that may vary in different segments of the wire, but the flexural strength at any one segment of the guidewire cannot be changed or adjusted after manufacture or during use in a patient.

A microtube guide according to the present disclosure is a unique "hybrid" concept that uses a microcatheter as the outer component of the guide and a free and movable central core as the inner component of the guide. The distal end of the microcatheter is closed, not open as in a typical catheter.

The central core may be tapered for a portion of its distal end, and by adjusting the depth of core insertion into the microcatheter, the stiffness of that segment of the guide may be adjusted. The depth of core insertion or retraction can also be used to change the configuration of the guide.

Because the central core drives the stiffness of the guide, cores can be exchanged for other cores having different stiffness, distal taper, or even core wire shape—all with the same outer tube (microcatheter). The core exchange can even be done during the procedure while the outer component of the guide is in the patient. The guide of the present disclosure thus provides the capability of changing wire support during a procedure without having to exchange the device.

Being able to adjust the depth of the core can change the configuration of the microtube guide. The shape of the distal end of the central core can be formed as desired by the thermoset process of the polyimide or other manufacturing processes. Advancing or retracting the core can vary this shape of the distal end. Exchanging the core for a stiff or softer, long taper or short taper, distal end can also change the guide's distal configuration or transport performance of the desired device.

In addition, having the outer surface of the device being a smooth microcatheter construction and not a wire wrapped core (as are most of our present guidewires) is less traumatic to the human tissues. In use with heart TAVR procedures, this characteristic should help prevent wire perforations of the heart or other damage.

In some embodiments, these "hybrid" devices will be constructed of a polyimide (or similar substance) microcatheter with or without braid as an outer component. Unlike currently-used microcatheters, the distal end will not be open to the patient. The size (OD) will vary upon the device application—coronary, peripheral, structural heart, cerebral, etc. The inner core will typically be a PTFE coated stainless steel wire or nitinol (but not limited to these).

Adjustment collars of the microtube may be used to hold the core position within the microtube, as discussed herein.

DESCRIPTION OF THE DRAWINGS

FIG. 3 depicts the guide of FIG. 1, showing the adjustment capability of the guide.

FIG. 4 depicts an exemplary adjustment collar for adjusting the guide.

DETAILED DESCRIPTION

Figure 1:
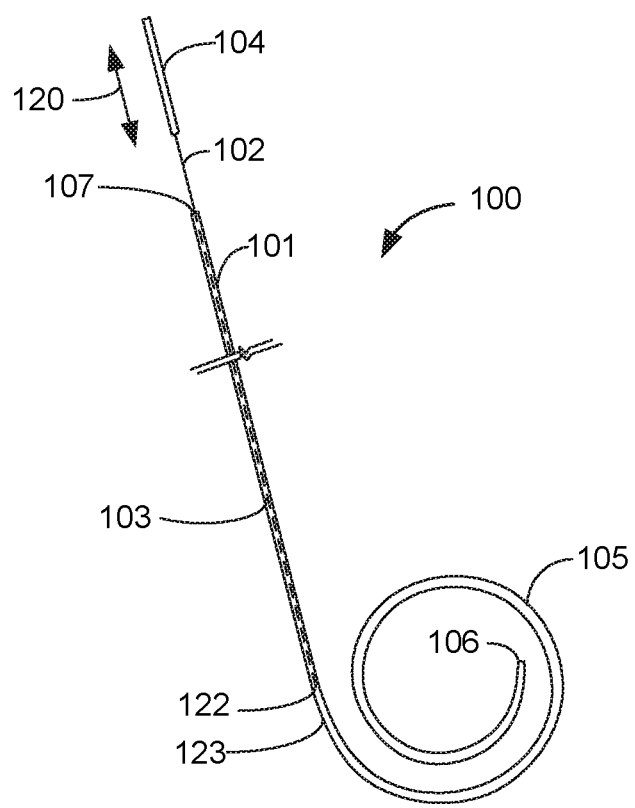
FIG. 1 depicts a microcatheter guide according to an exemplary embodiment of the present disclosure.

FIG. 1 depicts a microtube guide 100 comprising a microtube 101 combined with a free-floating and removable core 102 according to the present disclosure. The microtube 101 is a hollow microcatheter, formed from plastic in one embodiment. A proximal opening 107 of the microtube 101 receives the core 102, which slides within the microtube 101 to advance and retract in the direction indicated by directional arrow 120.

The microtube 101 comprises a generally straight main shaft 103 that is hollow to receive the core 102. The microtube 101 further comprises an expandable distal loop 105. The distal loop 105 is disposed at a distal end 106 of the microtube 101. The distal end 106 of the microtube is closed in the illustrated embodiment, and not open like typical microcatheters.

Figure 2:
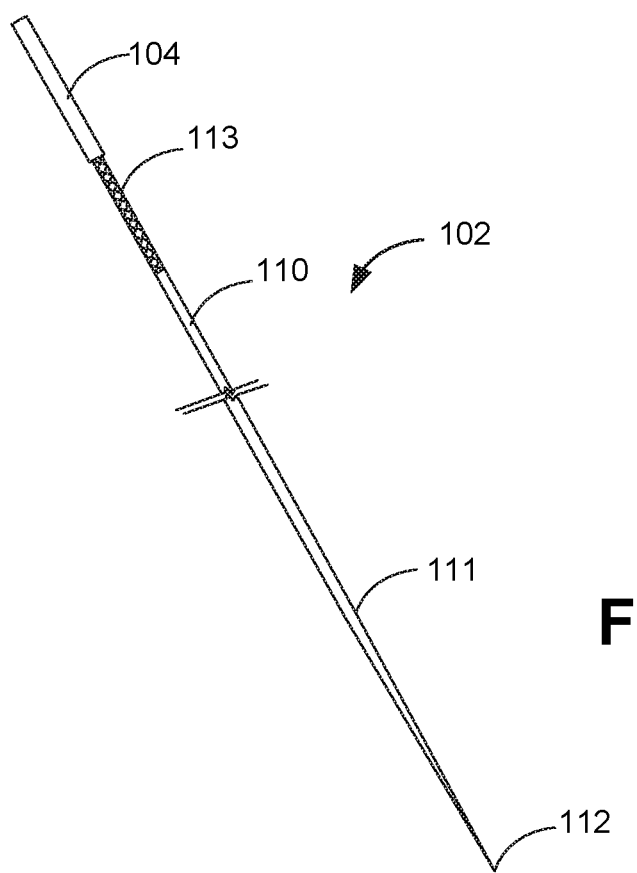
FIG. 2 depicts an exemplary core of the microcatheter guide according to an embodiment of the present disclosure.

The guide further comprises a proximal core end 104, which in the illustrated embodiment is a section of microcatheter tubing that is fixed to the core 102. The outer diameter of the proximal end is generally the same as the outer diameter of the microtube 101. When the guide is initially being fed into a patient's vessels, the core 102 may be fully advanced within the microtube 101, i.e., such that there is not an exposed section of core 102 as is shown in FIG. 2. The proximal core end 104 being formed from microcatheter tubing of the same diameter as the microtube 101 provides a smooth, gap-free outer surface of the guide 100 when the guide is being fed into the patient.

The main shaft 103 of the microtube 101 is formed from kink-resistant, thin-walled, semi-rigid plastic tube that is 0.035 inches in outer diameter in one embodiment. In other embodiments, the main shaft 103 is formed with braided steel within the plastic of the guidetube (polyimide braid, for example).

In one embodiment, the distal loop 105 is slightly larger in cross-sectional diameter than the main shaft 103, and formed from kink-resistant, semi-rigid plastic tubing that is the range of 0.045-0.054 inches in outer diameter. A transition portion (not shown) between the main shaft 103 and the distal loop 105 transitions the main shaft 103 to the distal loop 105 in one embodiment. In this regard, the main shaft 103 may be fused to the distal loop 105 at the transition portion.

The distal loop 105 being larger in diameter than the main shaft 103 helps to prevent excessive forward advancement of the valve delivery system (not shown) that delivers the replacement valve. In addition, the distal loop 105 being larger in diameter may simplify forming of the microtube 101. In this regard, the main shaft 103 may be fit within and be frictionally received by the distal loop 105 prior to fusing of the main shaft 103 to the distal loop 105.

The distal loop 105 is softer than the main shaft 103, and when not acted upon by an external catheter (not shown) or the core 102, the distal loop forms a loop as shown. In the illustrated embodiment, the body of the distal loop makes about one and one half loops. An outer diameter of the distal loop in this configuration may be about 3.0 centimeters.

When the core 102 is advanced such that its tip 122 (shown in dashed line) enters the distal loop 105, the tip 122 contacts an inner surface 123 of the distal loop 105 and causes the diameter of the distal loop 105 to increase. By advancing or retracting the core 102, the size of the distal loop 105 may be enlarged or decreased. Further, the distal loop 105 may fully straighten upon advancement of the core 102 as well.

Although FIG. 1 illustrates a distal loop 105 that extends downwardly from the guide, in other embodiments, the loop may be disposed horizontally to the microtube 101, i.e., perpendicular to the microtube 101, or otherwise oriented differently.

FIG. 2 depicts an enlarged view of an exemplary core 102 according to an embodiment of the present disclosure. The core 102 is advanced through the proximal opening 107 (FIG. 1) of the microtube 101.

The core 102 comprises a main shaft 110 and a tapered distal end 111. The main shaft 110 and the distal end 111 are formed from flexible polytetrafluoroethylene (PTFE) coated stainless steel in one embodiment. In this embodiment, the distal end 111 is smaller in diameter than the main shaft 110 and tapers from the diameter of the main shaft 110 to a distal tip 112. The distal tip 112 is received by the proximal opening 107 (FIG. 1) of the microtube 101 (FIG. 1) and advances into the distal loop 105 (FIG. 1) of the microtube 101.

As discussed above with respect to FIG. 1, the core 102 further comprises a proximal core end 104 that is a section of microcatheter tubing fixed to the main shaft 110 of the core 102. An adjustment section 113 of the core 102 is disposed adjacent to the proximal core end 104. In the illustrated embodiment, the adjustment section 113 is shown as textured (e.g., etched). The texture in the adjustment section may help the core 102 grip the inside of the microtube 101 (FIG. 1).

FIG. 3 depicts the guide 100 of FIG. 1, showing an exposed section 121 of the main shaft 110 of the core 102 between the microtube 101 and the proximal core end 104 of the guide 100. The proximal core end 104 is fixed to the main shaft 110 of the core 102, and the core 102 is received by and slides within the microtube 101. In a method for operating the guide 100, the user (not shown) advances the core 102 within the microtube 101 until the core 102 expands the distal loop 105 to the desired diameter. When the core 102 has been advanced as desired, the exposed section 121 of core 102 will be a length "L" as indicated in FIG. 3. At this point, a collar 130 (FIG. 4) of the same length "L" may be placed onto the exposed section 121, fitting over the core 102 between a lower end 135 of the proximal core end 104 and the proximal opening 107. The collar 130 serves to fix the core 102 within the microtube 101 such that it cannot advance further into the microtube 101.

FIG. 4 depicts an enlarged view of an exemplary collar 130 as discussed above with respect to FIG. 3. The collar 130 comprises a generally semi-cylindrical ("C"-shaped) section of microtubing of a length "L," with a slit 131 that is sized so that the collar 130 can fit over the main shaft 110 (FIG. 3) of the core 102 (FIG. 3). The collar 130 further comprises a proximal collar end 132 and a distal collar end 133. When the collar 130 is installed on the guide 100 (FIG. 3), the proximal collar end 132 is adjacent to and contacts the lower end 135 (FIG. 3) of the proximal core end 104 (FIG. 3), and the distal collar end 133 is adjacent to and contacts the proximal opening 107 (FIG. 3) of the microtube 101 (FIG. 3). The collar 130 may be any of various lengths "L," which lengths are determined by the lengths desired for the user to get the desired advancement of the core 102 within the microtube 101. Thus multiple collar lengths are available depending on the length desired by the user.

Figure 5:
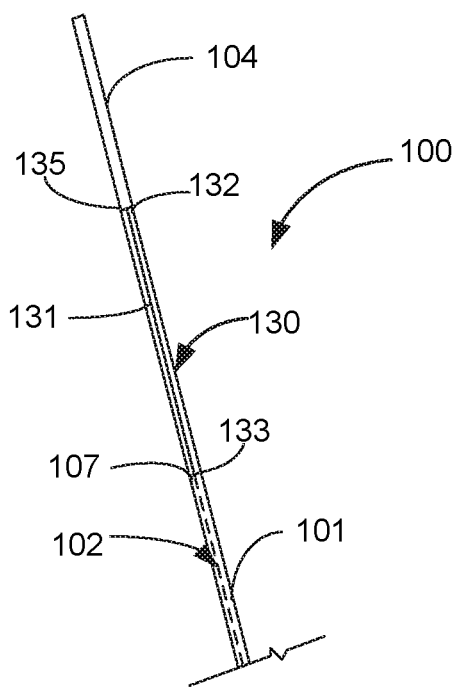
FIG. 5 depicts a partial view of the guide showing an adjustment collar installed over the core to set the distance the core is advanced within the microtube.

FIG. 5 depicts a partial view of the guide 100 with the collar 130 installed on the guide 100 to temporarily fix the length of the core 102 (shown in dashed line) that is advanced within the microtube 101. The collar 130 has an outer diameter that is generally the same as the microtube 101 and the proximal core end 104 of the core 120, such that when the collar 130 is installed, the outer surfaces of the proximal core end 104, the collar 130, and the microtube 101 are generally flush.

In an exemplary operation of the guide 100, the core 102 may initially be fully advanced into the microtube 101 such that the microtube 101 is generally straight, with no looped distal end. In this configuration, the lower end 135 of the proximal core end 104 is adjacent to and contacts the proximal opening 107 of the microtube 101. Two users (not shown) may be required to hold the guide 100 during installation and use due to the length of the guide 100. One user typically holds the proximal core end 104 of the core 102 while the other user maneuvers the distal end of the guide 100 into the patient. When the guide 102 is used in a TAVR procedure, for example, after the distal end of the microtube 101 crosses the valve, the person holding the proximal core end 104 may hold it steady while the other person advances the microtube 101 slightly to deploy the distal end 105 into a loop as discussed herein. When the distal end 105 is deployed as desired, a collar 130 of the desired length "L" can be installed in the now-exposed space between the lower end 135 of the proximal core end 104 and the proximal opening 107 of the microtube 101.

In other embodiments, the microtube (not shown) may not have a distal ring. Rather, the microtube may conform to a shape and stiffness of a core (not shown) that has some other shape.

This disclosure may be provided in other specific forms and embodiments without departing from the essential characteristics as described herein. The embodiments described are to be considered in all aspects as illustrative only and not restrictive in any manner.

The terms "first," "second," and the like are used herein to describe various features or elements, but these features or elements should not be limited by these terms. These terms are used only to distinguish one feature or element from another feature or element. Thus, a first feature or element discussed below could be termed a second feature or element, and similarly, a second feature or element discussed below could be termed a first feature or element without departing from the teachings of the present disclo-

What is claimed is:

1. A device comprising:
a generally hollow microtube comprising a tube shaft and a substantially-circular downwardly-extending distal ring, the tube shaft and the distal ring formed from flexible plastic tubing, the tube shaft comprising a proximal opening on a proximal end of the tube shaft and a closed distal end; and
a first core receivable by the proximal opening of the tube shaft of the microtube and slideable within the microtube, the first core comprising a proximal core end and a distal core end, the proximal core end comprising a section of microtubing fixed to the core, the distal core end comprising flexible wire, the distal core end stiffer than the distal ring of the guidetube such that advancing the distal core end within the microtube adjusts a shape of the downwardly-extending distal ring from a partially-deployed configuration when the first core is advanced partially into the distal ring to a deployed configuration when the first core is retracted from the distal ring, the distal ring formed within a single downwardly-extending plane.

2. The device of claim 1, wherein an outer diameter of the proximal core end is substantially the same as an outer diameter of the microtube.

3. The device of claim 1, the distal ring extending substantially 360 degrees around when the microtube is in a partially-deployed configuration and extending substantially 540 degrees around when the microtube is in the deployed configuration.

4. The device of claim 3, wherein the stiffness of the first core causes the distal ring to straighten when the first core is advanced fully into the microtube, and wherein the first core causes the distal ring of the microtube to deploy when the first core is retracted from the distal ring.

5. The device of claim 1, wherein the first core comprises a first flexural modulus.

6. The device of claim 5, further comprising a second core, the second core comprising a second flexural modulus, the microtube configured such that the first core can be removed from the microtube and the second core inserted into the microtube while the microtube is in place within a patient's body, the second core comprising a different flexibility from the first core.

7. A device comprising:
a generally hollow microtube comprising a tube shaft and a distal ring, the tube shaft and the distal ring formed from flexible plastic tubing, the tube shaft comprising a proximal opening on a proximal end of the tube shaft and a closed distal end;
a first core receivable by the proximal opening of the tube shaft of the microtube and slideable within the microtube, the first core comprising a proximal core end and a distal core end, the proximal core end comprising a section of microtubing fixed to the core, the distal core end comprising flexible wire, the microtube and the first core configured such that advancing the first core within the microtube adjusts a shape of the distal ring;
a first adjustment collar, the first adjustment collar comprising a semi-cylindrical tube segment with a longitudinal slit, the collar configured to fit over the first core between the proximal core end and the proximal opening of the microtube, the first adjustment collar having a first length, the collar further configured to prevent the first core from advancing further into the microtube when the first collar is installed on the microtube.

8. The device of claim 7, further comprising a second adjustment collar, the second adjustment collar comprising a semi-cylindrical tube segment with a longitudinal slit, the second adjustment collar configured to fit over the first core between the proximal core end and the proximal opening of the microtube, the second adjustment collar having a second length, the second length different from the first length, the second collar further configured to prevent the first core from advancing further into the microtube when the second collar is installed on the microtube.

\* \* \* \* \*